(12) United States Patent
Zhang et al.

(10) Patent No.: US 10,697,873 B2
(45) Date of Patent: Jun. 30, 2020

(54) METHOD FOR DETERMINING PHYSICAL SIMILARITY SIMULATION MATERIAL OF SOLID BACKFILL BODY

(71) Applicants: China University of Mining and Technology, Jiangsu (CN); XUZHOU ZHONAN SCIENCE&TECHNOLOGY CO., LTD, Jiangsu (CN); China Pingmei Shenma Energy and Chemical Industry Group Co., LTD, Henan (CN); Pingdingshan Tianan Coal Mining Co., LTD, Henan (CN)

(72) Inventors: Jixiong Zhang, Jiangsu (CN); Xiaole Han, Jiangsu (CN); Qiang Zhang, Jiangsu (CN); Lixin Lan, Jiangsu (CN); Yadong Chen, Jiangsu (CN); Yang Tai, Jiangsu (CN)

(73) Assignees: China University of Mining and Technology, Jiangsu (CN); XUZHOU ZHONAN SCIENCE&TECHNOLOGY CO., LTD, Jiangsu (CN); China Pingmei Shenma Energy and Chemical Industry Group Co., LTD, Henan (CN); Pingdinghsan Tianan Coal Mining Co., LTD, Henan (CN)

( * ) Notice: Subject to any disclaimer, the term of this patent is extended or adjusted under 35 U.S.C. 154(b) by 0 days.

(21) Appl. No.: 16/091,523

(22) PCT Filed: Nov. 16, 2017

(86) PCT No.: PCT/CN2017/111280
§ 371 (c)(1),
(2) Date: Oct. 5, 2018

(87) PCT Pub. No.: WO2018/166230
PCT Pub. Date: Sep. 20, 2018

(65) Prior Publication Data
US 2020/0003667 A1    Jan. 2, 2020

(30) Foreign Application Priority Data

Mar. 16, 2017  (CN) .......................... 2017 1 0156494

(51) Int. Cl.
*G01N 3/08* (2006.01)
*E21B 49/00* (2006.01)
(Continued)

(52) U.S. Cl.
CPC ............. *G01N 3/08* (2013.01); *E21B 49/006* (2013.01); *G01N 33/24* (2013.01); *G09B 25/06* (2013.01); *G01N 2203/0676* (2013.01)

(58) Field of Classification Search
CPC .. G01N 3/08; G01N 33/24; G01N 2203/0676; E21B 49/06; G09B 25/06
See application file for complete search history.

(56) References Cited

U.S. PATENT DOCUMENTS

2007/0183936 A1    8/2007  Newsam et al.

FOREIGN PATENT DOCUMENTS

| CN | 101221709 | 7/2008 |
| CN | 103758538 | 4/2014 |

(Continued)

OTHER PUBLICATIONS

"International Search Report (Form PCT/ISA/210)", dated Feb. 27, 2018, pp. 1-5.

*Primary Examiner* — David Z Huang
(74) *Attorney, Agent, or Firm* — JCIPRNET

(57) ABSTRACT

A method for determining a physical similarity simulation material of a solid backfill body is provided. A compaction test is run on a gangue backfill body in a lab, to obtain a $\varepsilon$-$\sigma$ curve regarding the gangue backfill body in the compaction process. Backfill blocks are made by using a thin wood board, sponge, and a paper sheet in different proportions, and then an unconfined compression test is separately run on the backfill blocks used for physical similarity simulation, to (Continued)

obtain $\varepsilon_i$-$\sigma_i$ curves regarding the backfill blocks in the compression process. A sum of squared errors $\Sigma(\varepsilon_i-\varepsilon_0)^2$ is introduced to separately calculate a sum of squared errors of the backfill block and that of the gangue backfill body, and accordingly an error between $\varepsilon$-$\sigma$ curves regarding the test block and the gangue backfill body is determined. Finally, a backfill block for which the sum of squared errors is less than 0.5 is determined as a physical similarity simulation material of the gangue backfill body. By fabrication and selection of similar materials, the present invention can reduce an error caused by a selected backfilling material during a physical similarity simulation experiment, guaranteeing the accuracy of the physical similarity simulation experiment for solid backfill mining.

6 Claims, 2 Drawing Sheets

(51) Int. Cl.
    *G01N 33/24*     (2006.01)
    *G09B 25/06*     (2006.01)

(56) References Cited

FOREIGN PATENT DOCUMENTS

| | | |
|---|---|---|
| CN | 103940669 | 7/2014 |
| CN | 104390861 | 3/2015 |
| CN | 104568593 | 4/2015 |
| CN | 106198232 | 12/2016 |
| CN | 107014680 | 8/2017 |

METHOD FOR DETERMINING PHYSICAL SIMILARITY SIMULATION MATERIAL OF SOLID BACKFILL BODY

CROSS-REFERENCE TO RELATED APPLICATION

This application is a 371 of international application of PCT application serial no. PCT/CN2017/111280, filed on Nov. 16, 2017, which claims the priority benefit of China application no. 201710156494.6, filed on Mar. 16, 2017. The entirety of each of the abovementioned patent applications is hereby incorporated by reference herein and made a part of this specification.

BACKGROUND

Technical Field

The present invention relates to the field of experimental technologies of backfill mining, and in particular, to a fully mechanized method for determining a physical similarity simulation material of a solid backfill body.

Description of Related Art

With the wide application of fully mechanized solid backfill mining technology in our country, surrounding rock control for overlying strata has been intensively studied. The main methods for studying the movement law of the overlying strata include physical similarity simulation, theoretical analysis, and numerical simulation, among which the physical similarity simulation method is considered as the most direct and effective one. The mechanical properties of a solid backfilling material decisively affect the success of backfill mining technology. If the mechanical properties of the solid backfilling material can be precisely simulated, a control of a solid backfill body over the overlying strata in actual status in the scene can be thoroughly reflected, and the experiment precision can be greatly enhanced. Thus, selection of a solid backfilling material in actual production and an improvement to a backfilling method can be optimized in the future. Therefore, it is highly necessary to develop a method for determining a physical similarity simulation material of the solid backfill body.

SUMMARY

In view of the shortcomings in the prior art, the present invention provides a simple, high-precision, secure and reliable method for determining a physical similarity simulation material of a solid backfill body.

The present invention relates to a method for designing a backfill-mining mass ratio in solid backfill mining, including the following steps:

a running a compaction test on a gangue backfill body by using a servo testing machine, recording values of stress $\sigma$ and strain $\varepsilon$ in a loading process, and drawing a $\varepsilon_0$-$\sigma_0$ curve 1 regarding the gangue backfill body in the compaction process as a reference curve;

b. setting the excavation height of a physical similarity model to h, and the excavation step to s, to obtain the height of a backfill block $h_1$=h/n, where the coefficient n in the equation is a real number not less than 1, that is, the height of the backfill block is less than or equal to the excavation height of the model;

c. designing dimensions of the backfill block: setting the length to the excavation step s, the width to that of the physical similarity model, and the height to the excavation height h of the physical similarity model;

d. selecting two categories of materials as a category-1 combined block and a category-2 combined block of the backfill block, separately cropping the two categories of materials according to the dimensions of the backfill block, separately piling up the two categories of materials till the respective aggregate thickness reaches the designed height of a backfill body, and recording the number K of pieces in each material category when the designed height is reached;

e. running an unconfined compression test:

running an unconfined compression test on the category-1 combined block by using the servo testing machine, recording stress $\sigma$ and strain $\varepsilon$ in a loading process, and drawing a $\varepsilon_1$-$\sigma_1$ curve 2 regarding the combined block of sponge and a thin wood board in the compression process; and running an unconfined compression test on the category-2 combined block by using the servo testing machine, recording stress $\sigma$ and strain $\varepsilon$ in a loading process, and drawing a $\varepsilon_2$-$\sigma_2$ curve 3 regarding the combined block of sponge, a thin wood board, and a common paper sheet in the compression process; and f. marking twenty equally-spaced points on a coordinate horizontal axis, separately calculating a sum of squared errors between the $\varepsilon_0$-$\sigma_0$ curve 1 and the $\varepsilon_1$-$\sigma_1$ curve 2, and that between the $\varepsilon_0$-$\sigma_0$ curve 1 and the $\varepsilon_2$-$\sigma_2$ curve 3, and selecting a combined block corresponding to the curve meeting an expression of $\Sigma(\varepsilon_i-\varepsilon_0)^2 \leq 0.5$ as a physical similarity simulation material of a solid backfill body; or if neither of the curves meets the expression of $\Sigma(\varepsilon_i-\varepsilon_0)^2 \leq 0.5$, increasing the number of pieces of the sponge to K+1, K+2, K+3, . . . , or K+i, till a curve meeting the expression of $\Sigma(\varepsilon_i-\varepsilon_0)^2 \leq 0.5$ is selected out.

The two categories of materials are described as follows: One category is formed by sponge and a thin wood board, where the sponge is fastened on the thin wood board with a transparent tape, to make the aggregate thickness of a backfill block formed by the sponge and thin wood board equal to $h_1$; and the other one is formed by sponge, a common paper sheet, and a thin wood board, where the sponge is fastened on the thin wood board with a transparent tape, to make the aggregate thickness of a backfill block formed by the sponge and thin wood board equal to $h_1/2$, and then the cropped common paper sheet is fixed on the backfill block formed by the sponge and thin wood board, to make the aggregate thickness of a backfill block formed by the sponge, thin wood board, and common paper sheet equal to $h_1$.

The sponge is ordinary sponge with the thickness of 1.5 cm to 2.5 cm.

The thickness of the thin wood board is about 2 mm to 4 mm.

The common paper sheet is common A4 printing paper.

The excavation height h of the physical similarity model is not greater than 5 cm in general cases.

The beneficial effects are as follows: By use of the foregoing technical solutions, the present invention can reduce an error caused by a selected backfilling material during a physical similarity simulation experiment, and also can correctly design the thickness of similar materials such as sponge, a thin wood board, and a paper sheet, guaranteeing the accuracy of the physical similarity simulation experiment for solid backfill mining.

DETAILED DESCRIPTION OF EMBODIMENTS

Figure 1:
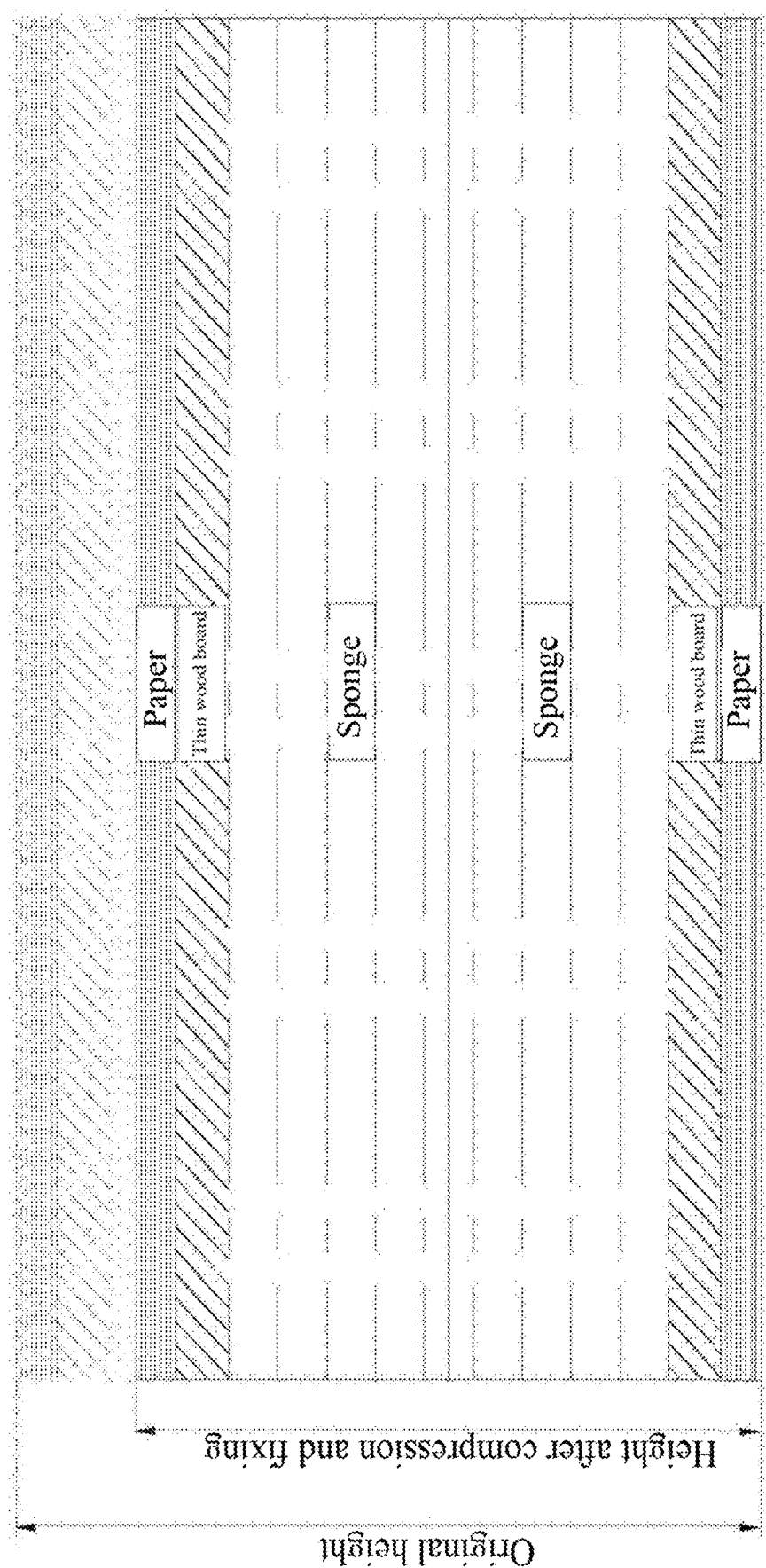
FIG. 1 is a schematic diagram showing fabrication of a physical similarity simulation material of a solid backfill body according to the present invention.
Figure 2:
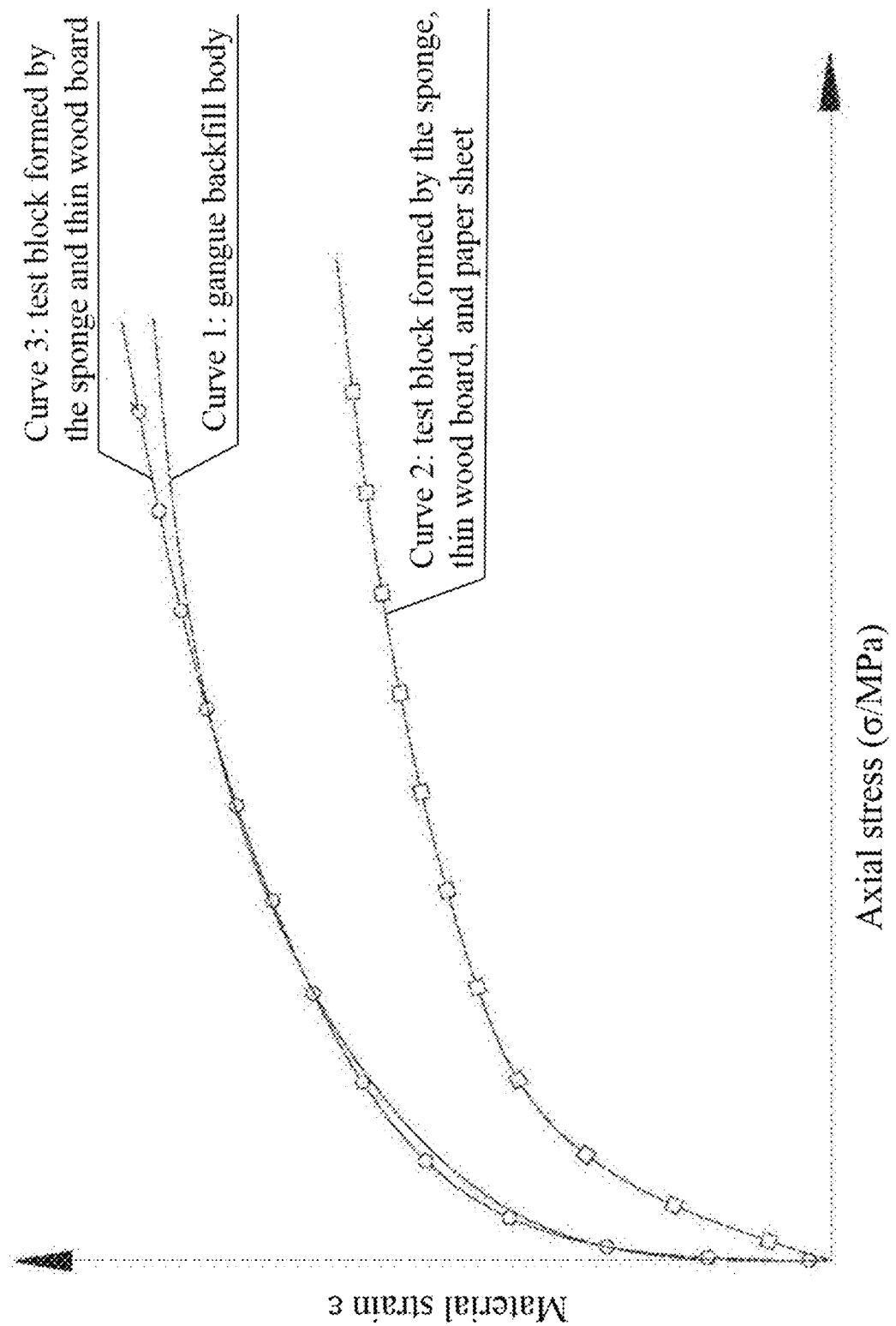
FIG. 2 shows stress-strain curves in a compaction process of solid backfilling materials according to an instance of the present invention.

Embodiments of the present invention are further described below with reference to the accompanying drawings:

Embodiment 1

In a method for determining a physical similarity simulation material of a solid backfill body of the present invention, a test block of the physical similarity simulation material is fabricated using different combinations of sponge, a thin wood board, and a common paper sheet, and a compression test is run on the test block and an actual solid backfilling material separately with a servo testing machine. Afterwards, data is processed by making a map, to find out a simulation material that is closest to the actual solid backfilling material.

a. A compaction test is run on a gangue backfill body (selected from backfill gangue in a coal mine) by using the servo testing machine, stress σ and strain ε in a loading process are recorded, and a $\varepsilon_0$-$\sigma_0$ curve 1 regarding the gangue backfill body in the compaction process is drawn as a reference curve.

b. According to dimensions of a paved physical similarity model, it is determined that the excavation height of the model is h, and the excavation step thereof is s, to obtain the height of a backfill block $h_1=h/n$, where n in the equation is a real number not less than 1, that is, the height of the backfill block is less than or equal to the excavation height of the model.

c. Dimensions of the backfill block are designed as follows: setting the length to the excavation step s, the width to that of the physical similarity model, and the height to the excavation height h of the model. Original materials including sponge, a thin wood board, a common paper sheet, and a transparent tape are acquired. Then, the sponge, thin wood board, and common paper sheet are cropped according to the dimensions of the backfill block.

d. The sponge is naturally piled up till its cumulative height is greater than the designed height $h_1$ of the backfill block, and the number K of pieces of the sponge in this case is recorded.

e. The backfill block is designed to include two categories. One category is formed by the sponge and thin wood board, where a sponge combination is fastened on the thin wood board with the transparent tape, to make the aggregate thickness of a backfill block formed by the sponge and thin wood board equal to $h_1$. The other one is formed by the sponge, common paper sheet, and thin wood board, where a sponge combination is fastened on the thin wood board with the transparent tape, to make the aggregate thickness of a backfill block formed by the sponge and thin wood board equal to $h_1/2$, and then the cropped common paper sheet is fixed on the backfill block formed by the sponge and thin wood board, to make the aggregate thickness of a backfill block formed by the sponge, thin wood board, and common paper sheet equal to $h_1$.

f. An unconfined compression test is run with the servo testing machine on the backfill block formed by the sponge and thin wood board, stress σ and strain ε in a loading process are recorded, and a $\varepsilon_1$-$\sigma_1$ curve 2 regarding the backfill block formed by the sponge and thin wood board in the compression process is drawn. An unconfined compression test is run with the servo testing machine on the combined block of the sponge, thin wood board, and common paper sheet, stress σ and strain ε in a loading process are recorded, and a $\varepsilon_2$-$\sigma_2$ curve 3 regarding the combined block of the sponge, thin wood board, and common paper sheet in the compression process is drawn.

g. Twenty equally-spaced points are marked on a coordinate horizontal axis, and a sum of squared errors between the curves 1 and 2 and that between the curves 1 and 3 are calculated separately. After calculation, it is learned that the sum of squared errors between the curves 1 and 2 is less than 0.5. Therefore, a combined block corresponding to the curve 2 is selected as the physical similarity simulation material of the solid backfill body.

Embodiment 2

A method for determining a physical similarity simulation material of a solid backfill body of the present invention includes the following steps.

a. A compaction test is run on a gangue backfill body (selected from backfill gangue in a coal mine) by using a servo testing machine, stress σ and strain ε in a loading process are recorded, and a $\varepsilon_0$-$\sigma_0$ curve 1 regarding the gangue backfill body in the compaction process is drawn as a reference curve.

b. According to dimensions of a paved physical similarity model, it is determined that the excavation height of the model is h, and the excavation step thereof is s, to obtain the height of a backfill block $h_1=h/n$, where n in the equation is a real number not less than 1, that is, the height of the backfill block is less than or equal to the excavation height of the model.

c. Dimensions of the backfill block are designed as follows: setting the length to the excavation step s, the width to that of the physical similarity model, and the height to the excavation height h of the model. Original materials including sponge, a thin wood board, a common paper sheet, and a transparent tape are acquired. Then, the sponge, thin wood board, and common paper sheet are cropped according to the dimensions of the backfill block.

d. The sponge is naturally piled up till its cumulative height is greater than the designed height $h_1$ of the backfill block, and the number K of pieces of the sponge in this case is recorded.

e. The backfill block is designed to include two categories. One category is formed by the sponge and thin wood board, where a sponge combination is fastened on the thin wood board with the transparent tape, to make the aggregate thickness of a backfill block formed by the sponge and thin wood board equal to $h_1$. The other one is formed by the sponge, common paper sheet, and thin wood board, where a sponge combination is fastened on the thin wood board with the transparent tape, to make the aggregate thickness of a combined block of the sponge and thin wood board equal to $h_1/2$, and then the cropped common paper sheet is fixed on the backfill block formed by the sponge and thin wood board, to make the aggregate thickness of a backfill block formed by the sponge, thin wood board, and common paper sheet equal to $h_1$.

f. An unconfined compression test is run with the servo testing machine on the combined block of the sponge and thin wood board, stress σ and strain ε in a loading process are recorded, and a $\varepsilon_1$-$\sigma_1$ curve 2 regarding the combined block of the sponge and thin wood board in the compression process is drawn. An unconfined compression test is run with the servo testing machine on the combined block of the sponge, thin wood board, and common paper sheet, stress σ and strain ε in a loading process are recorded, and a $\varepsilon_2$-$\sigma_2$ curve 3 regarding the combined block of the sponge, thin wood board, and common paper sheet in the compression process is drawn.

g. Twenty equally-spaced points are marked on a coordinate horizontal axis, a sum of squared errors between the curves 1 and 2 and that between the curves 1 and 3 are calculated separately, and a combined block corresponding to the curve meeting an expression of $\Sigma(\varepsilon_i-\varepsilon_0)^2 \leq 0.5$ is selected as a physical similarity simulation material of a solid backfill body.

h. If neither of the curves meets the expression of $\Sigma(\varepsilon_i-\varepsilon_0)^2 \leq 0.5$, the number of pieces of the sponge is increased to K+1, K+2, K+3, . . . ; and steps d to g are repeated till a backfill block meeting the expression of $\Sigma(\varepsilon_i-\varepsilon_0)^2 \leq 0.5$ is selected out.

Among the original materials, the sponge is ordinary sponge with the thickness of about 2 cm; the thickness of the thin wood board is about 3 mm; and the common paper sheet is common A4 printing paper.

The excavation height of the physical similarity model of the solid backfill body is not greater than 5 cm in general cases.

What is claimed is:

1. A method for designing a backfill-mining mass ratio in solid backfill mining, comprising the following steps:
    running a compaction test on a gangue backfill body by using a servo testing machine, recording values of stress σ and strains in a loading process of the compaction test, and drawing a $\varepsilon_0$-$\sigma_0$ curve 1 regarding the gangue backfill body in a compaction process as a reference curve;
    setting an excavation height of a physical similarity model to h, and an excavation step to s, to obtain a height of a backfill block $h_1$=h/n, wherein coefficient n is a real number not less than 1, the height of the backfill block is less than or equal to the excavation height of the physical similarity model;
    designing dimensions of the backfill block: setting a length to the excavation step s, a width to a width of the physical similarity model, and a height to the excavation height h of the physical similarity model;
    selecting two categories of materials as a category-1 combined block and a category-2 combined block of the backfill block, separately cropping the two categories of materials according to the dimensions of the backfill block, separately piling up the two categories of materials until a respective aggregate thickness reaches a designed height of a backfill body, and recording a number K of pieces in each material category when the designed height is reached;
    running an unconfined compression test, comprising:
        running the unconfined compression test on the category-1 combined block by using the servo testing machine, recording stress σ and strain ε in a loading process of the unconfined compression test on the category-1 combined block, and drawing a $\varepsilon_1$-$\sigma_1$ curve 2 regarding the category-1 combined block of a first sponge and a first thin wood board; and
        running the unconfined compression test on the category-2 combined block by using the servo testing machine, recording stress σ and strain ε in a loading process of the unconfined compression test on the category-2 combined block, and drawing a $\varepsilon_2$-$\sigma_2$ curve 3 regarding the category-2 combined block of a second sponge, a second thin wood board, and a paper sheet; and
    marking twenty equally-spaced points on a coordinate horizontal axis, separately calculating a sum of squared errors between the $\varepsilon_0$-$\sigma_0$ curve 1 and the $\varepsilon_1$-$\sigma_1$ curve 2, and a sum of squared errors between the $\varepsilon_0$-$\sigma_0$ curve 1 and the $\varepsilon_2$-$\sigma_2$ curve 3, and selecting one of the category-1 combined block and the category-2 combined block, which meets an expression of $\Sigma(\varepsilon_i-\varepsilon_0)^2 \leq 0.5$, wherein i=1 or 2, as a physical similarity simulation material of a solid backfill body; or
    if none of the $\varepsilon_1$-$\sigma_1$ curve 2 and the $\varepsilon_2$-$\sigma_2$ curve 3 meets the expression of $\Sigma(\varepsilon_i-\varepsilon_0)^2 \leq 0.5$, increasing the number of pieces of the first and second sponges until the one of the category-1 combined block and the category-2 combined block which meets the expression of $\Sigma(\varepsilon_i-\varepsilon_0)^2 \leq 0.5$ is selected out.

2. The method for designing a backfill-mining mass ratio in solid backfill mining according to claim 1, wherein the two categories of materials are as follows: one category is formed by the first sponge and the first thin wood board, the first sponge being fastened on the first thin wood board with a first transparent tape, to make the aggregate thickness of the backfill block formed by the first sponge and the first thin wood board equal to $h_1$; and the other category is formed by the second sponge, the paper sheet, and the second thin wood board, the second sponge being fastened on the second thin wood board with a second transparent tape, to make the aggregate thickness of the backfill block formed by the second sponge and the second thin wood board equal to $h_1/2$, and then the paper sheet being cropped and fixed on the backfill block formed by the second sponge and the second thin wood board, to make the aggregate thickness of the backfill block formed by the second sponge, the second thin wood board, and the paper sheet equal to $h_1$.

3. The method for designing a backfill-mining mass ratio in solid backfill mining according to claim 2, wherein the first or second sponge has a thickness of 1.5 cm to 2.5 cm.

4. The method for designing a backfill-mining mass ratio in solid backfill mining according to claim 2, wherein the thickness of the first or second thin wood board is 2 mm to 4 mm.

5. The method for designing a backfill-mining mass ratio in solid backfill mining according to claim 2, wherein the paper sheet is A4 printing paper.

6. The method for designing a backfill-mining mass ratio in solid backfill mining according to claim 1, wherein the excavation height h of the physical similarity model is not greater than 5 cm.

* * * * *

UNITED STATES PATENT AND TRADEMARK OFFICE
CERTIFICATE OF CORRECTION

PATENT NO. : 10,697,873 B2
APPLICATION NO. : 16/091523
DATED : June 30, 2020
INVENTOR(S) : Jixiong Zhang et al.

It is certified that error appears in the above-identified patent and that said Letters Patent is hereby corrected as shown below:

On the Title Page

Item (72) Inventors, should read as:
Jixiong ZHANG, Jiangsu (CN);
Xiaole HAN, Jiangsu (CN);
Jianguo ZHANG, Henan (CN);
Qiang Zhang, Jiangsu (CN);
Shu qi Pan, Henan (CN);
Lixin Lan, Jiangsu (CN);
Yadong Chen, Jiangsu (CN);
Yang Tai, Jiangsu (CN)

Signed and Sealed this
Twenty-second Day of December, 2020

Andrei Iancu
*Director of the United States Patent and Trademark Office*